United States Patent
Abboud et al.

(10) Patent No.: US 6,468,268 B1
(45) Date of Patent: Oct. 22, 2002

(54) CRYOGENIC CATHETER SYSTEM

(75) Inventors: Marwan Abboud, Pierrefonds; Johnny Al Asmar, Montréal; Jean-Pierre Lalonde, Verdun, all of (CA)

(73) Assignee: CryoCath Technologies Inc., Kirkland (CA)

( * ) Notice: Subject to any disclaimer, the term of this patent is extended or adjusted under 35 U.S.C. 154(b) by 0 days.

(21) Appl. No.: 09/489,644

(22) Filed: Jan. 24, 2000

Related U.S. Application Data

(60) Provisional application No. 60/117,175, filed on Jan. 25, 1999.

(51) Int. Cl.[7] .............................................. A61B 18/18
(52) U.S. Cl. .............................. 606/20; 606/22; 606/21
(58) Field of Search ...................................... 606/20–23

(56) References Cited

U.S. PATENT DOCUMENTS

| | | | |
|---|---|---|---|
| 3,823,575 A | * 7/1974 | Parel | 606/24 |
| 3,859,986 A | 1/1975 | Okada et al. | 128/7 |
| 4,522,194 A | 6/1985 | Normann | |
| 5,423,807 A | * 6/1995 | Milder | 606/20 |
| 5,651,780 A | 7/1997 | Jackson et al. | |
| 5,658,278 A | 8/1997 | Imran et al. | |
| 5,674,218 A | 10/1997 | Rubinsky et al. | |
| 5,743,903 A | 4/1998 | Stern et al. | |
| 5,759,182 A | 6/1998 | Varney et al. | 606/21 |
| 6,019,783 A | 2/2000 | Philips et al. | |
| 6,027,500 A | 2/2000 | Buckles et al. | |
| 6,106,518 A | * 8/2000 | Wittenberger et al. | 606/23 |

FOREIGN PATENT DOCUMENTS

| | | |
|---|---|---|
| EP | 0 651 308 A | 5/1995 |
| GB | 2 026 324 | 2/1980 |
| WO | 96/30816 | 10/1996 |
| WO | 98/37822 | 9/1998 |
| WO | 99/56639 | 11/1999 |
| WO | 99/56640 | 11/1999 |
| WO | 99/56641 | 11/1999 |
| WO | 00/35362 | 6/2000 |

* cited by examiner

Primary Examiner—Roy D. Gibson
(74) Attorney, Agent, or Firm—Christopher & Weisberg, P.A.

(57) ABSTRACT

A cryogenic catheter system provides safe and effective treatment of tissue. The system includes a catheter that is coupled to a console via fluid and electrical umbilicals. The console controls the overall operation of the system based to provide and maintain a predetermined temperature at the catheter tip. The console also controls and monitors operating parameters for providing warning indications to the user and terminating operation of the system in the event of a failure that may compromise patient safety.

2 Claims, 13 Drawing Sheets

CRYOGENIC CATHETER SYSTEM

CROSS REFERENCE TO RELATED APPLICATION

This application claims priority from U.S. Provisional Patent Application No. 60/117,175, filed on Jan. 25, 1999.

STATEMENT REGARDING FEDERALLY SPONSORED RESEARCH

Not Applicable.

1. Field of the Invention

The present invention relates to tissue ablation, and more particularly, to cryogenic catheter systems.

2. Background of the Invention

Many medical procedures are performed using minimally invasive surgical techniques where one or more slender implements are inserted through a small incision into a patient's body. Minimally, invasive surgical implements for ablating tissue can include a rigid or flexible structure having an ablation device at or near its distal end that is placed adjacent to the tissue to be ablated.

There are many procedures that include ablating certain tissue. For example, cardiac arrhythmias can be treated through selective ablation of cardiac tissue to eliminate the source of the arrhythmia. One type of minimally invasive procedure includes the use of an ablation catheter subsequent to a preliminary step of electrocardiographic mapping. After examination of the mapping results, one or more ablated regions (lesions) are created in the cardiac tissue.

A number of cooled catheter systems (cryocatheters) have been developed for treating tissue in a cardiac setting, either to cool the tissue sufficiently to stun it and allow cold mapping of the heart and/or confirmation of catheter position with respect to localized tissue lesions, or to apply a more severe level of cold to ablate tissue at the site of the catheter ending. In general, the range of treatments which may be effected by a cryocatheter is comparable to the range of applications for RF or thermal ablation catheters, and in particular, these instruments may be configured to achieve either small localized ball shape lesions at the tip of the catheter, or one or more elongated linear lesions extending a length of several centimeters or more along the tip. Elongate lesions are commonly used to achieve conduction block across a region of the cardiac wall so as to sever a re-entrant pathway, thereby preventing conduction across the region, in order change the cardiac signal path topology. For example, it may be desired to eliminate a re-entrant pathway responsible for atrial fibrillation or a tachycardia.

In general, when used for endovascular access to treat the cardiac wall, for example, catheters of this type must meet fairly demanding limitations regarding their size, flexibility, strength, electrical conductivity and the like which affect their safety. These constraints generally require that the catheter be no larger than several millimeters in diameter so as to pass through the vascular system of the patient to the heart. Thus, any electrodes (in the case of mapping or RF/electrothermal ablation catheters), and any coolant passages (in the case of cryocatheters) must fit within a catheter body of small size.

In addition, there are important safety considerations when using cryogenic catheters for non-invasive procedures. For example, the cryogenic fluid used to cool the catheter tip may leak so as to enter the patient's body. Further, a vacuum used to exhaust spent fluid may remove blood from the patient into the fluid recovery reservoir. In addition, a particular procedure may have to be aborted prematurely without achieving the desired therapeutic effect if the cryocatheter system has insufficient coolant.

Furthermore, it may be desirable to treat tissue using a predetermined time and temperature schedule. However, manually timing the length of a procedure and repeatedly adjusting the tip temperature can lead to operator error, as well as inefficient treatment of the tissue. That is, the applied cryogenic energy may not be applied so as to maximize tissue destruction. In addition, the actual tip temperature may be different than a selected temperature due to thermal variations at the treatment site.

It would, therefore, be desirable to provide a cryogenic catheter system that controls and monitors operating parameters, automatically if desired, to achieve safe and effective cryogenic treatment of tissue.

SUMMARY OF THE INVENTION

The present invention provides a cryogenic catheter system that controls and monitors mechanical and electrical operating parameters of the system to ensure safe and optimal treatment of tissue. The cryogenic system includes a catheter for treating tissue, a console for controlling overall system operation, and an umbilical system for providing refrigerant and electrical paths between the catheter and the console.

The catheter can be a spot-type with a rounded tip for creating a relatively round, concentrated region of destroyed tissue. Alternatively, the catheter can be a linear-type to create an elongate lesion. In general, liquid coolant flows from the console via an inlet path in a mechanical umbilical. The pressurized coolant evaporates in the catheter tip to cool the tip to a predetermined temperature. The spent coolant returns to the console under vacuum via a return path in the mechanical umbilical. The coolant is compressed and captured in a recovery tank.

The console controls and monitors system operation to provide safe and effective treatment of a patient. The console includes a user interface to allow selection of manual mode or automatic mode, which sets the catheter to a desired time and temperature treatment schedule. The console controls the catheter tip temperature by monitoring the actual tip temperature, by means of a thermocouple for example, and adjusting the coolant injection pressure as needed to achieve the desired tip temperature.

The console also monitors system operational parameters to ensure that patient safety is not compromised. The console determines whether a detected fault is a warning condition, which may allow a procedure to continue, or is a failure condition, in which case the injection of coolant should be stopped. In general, any fault that compromises patient safety results in a failure condition that terminates the procedure.

The system can also include a leak detection system for detecting the presence of foreign liquid, such as blood, within the closed coolant path. In an exemplary embodiment, the leak detection system includes a first sensor located in the catheter tip and a second sensor disposed within the catheter handle. The leak detection system can include a third sensor in the console for preventing a blood from reaching the vacuum pump.

BRIEF DESCRIPTION OF THE DRAWINGS

The invention will be more fully understood from the following detailed description taken in conjunction with the accompanying drawings, in which.

DETAILED DESCRIPTION OF INVENTION

Figure 1:
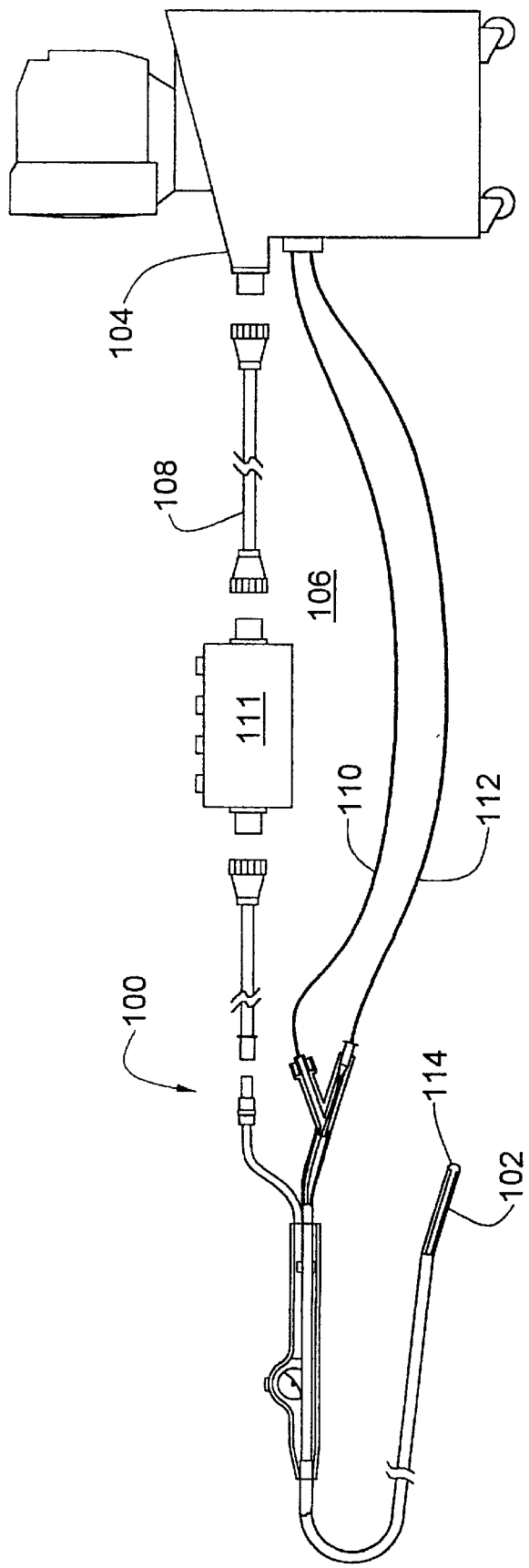
FIG. 1 is a diagrammatic depiction of a cryogenic catheter system in accordance with the present invention.

FIG. 1 shows a cryogenic catheter system 100 in accordance with the present invention. The system 100 includes a treatment catheter 102 coupled to a console 104 via an umbilical system 106. The umbilical system includes an electrical umbilical 108 that contains signal lines for cardiac monitoring and/or mapping that are ultimately coupled to a an ECG monitor. The electrical umbilical 108 can include an ECG box 111 to facilitate a connection from ring electrodes 116 (FIGS. 2A–B) to the ECG monitor. A coolant injection umbilical 112 and a coolant vacuum umbilical 110 provide respective inlet and return paths for a refrigerant or coolant used to cool a tissue-treating end 114 of the catheter. The console 104 provides a user interface to the system and houses the electronics and software for controlling and recording the ablation procedure, for controlling delivery of liquid refrigerant under high pressure through the umbilical to the catheter, for controlling the recovery of the expanded refrigerant vapor from the catheter under vacuum, and for controlling a compressor to pressurize the coolant vapor into a liquid stored in a recovery tank.

The cryoablation system 100 produces controlled cryogenic temperatures at the tip of a family of long, flexible catheters which can be inserted through various passages of the body. One application of the system is delivering cold to the inner walls of a beating heart by approaching the heart through the body's vasculature from punctures in the skin. This procedure is done to correct electrophysiological abnormalities leading to irregular or errant heartbeats. It selectively destroys (ablates) the electrical characteristics of groups of heart cells (arrhythmogenic sites) which cause or propagate the abnormality. However, the cyroablation system 100 can be used for any procedure that benefits from the application of extreme cold to tissue, and is therefore not limited to cardiac procedures.

Figure 2A:
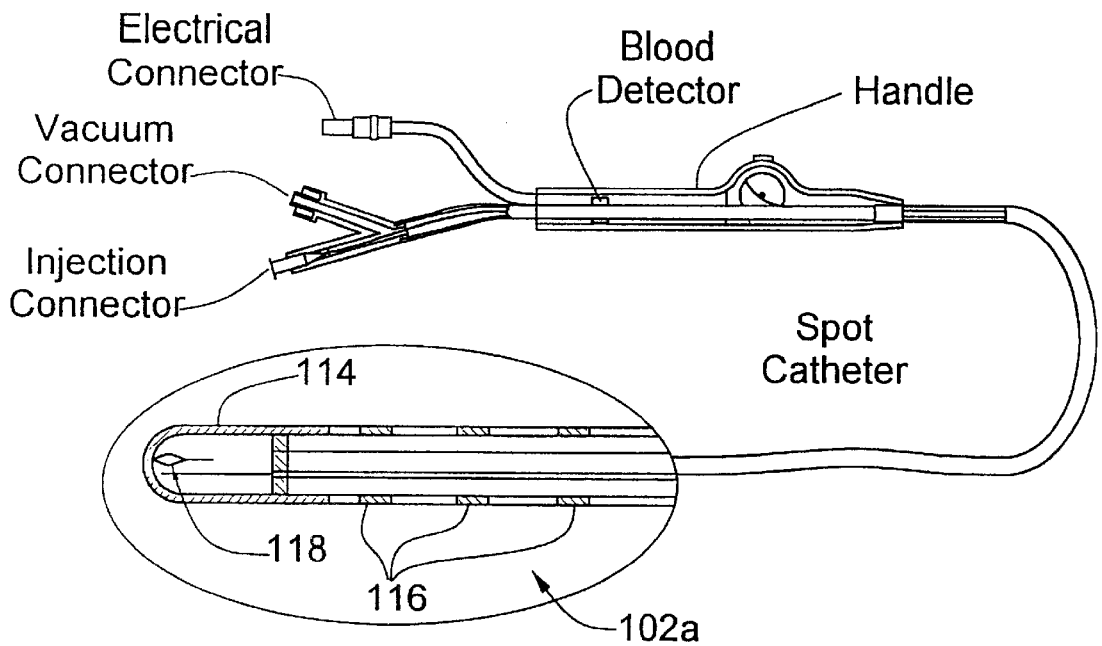
FIG. 2A is a detailed view of a spot-type catheter forming a part of the system of FIG. 1.
Figure 2B:
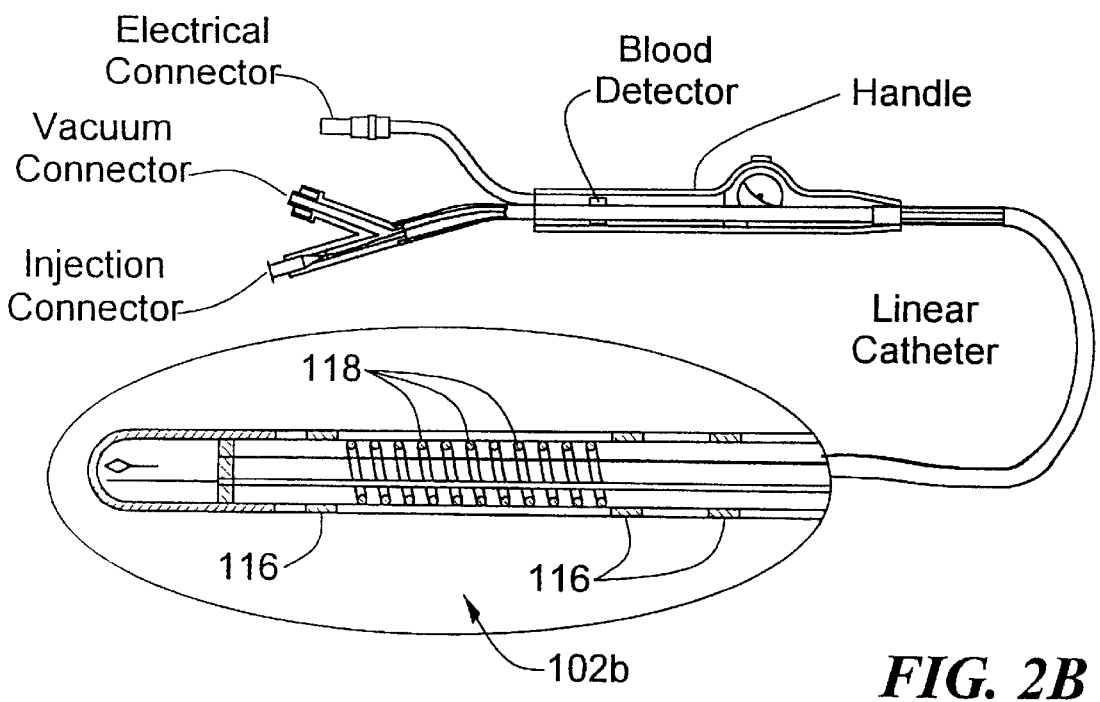
FIG. 2B is a detailed view of a linear-type catheter forming a part of the system of FIG. 1.

FIGS. 2A–B show two exemplary catheters in a family of sterile disposable catheters. FIG. 2A shows a "spot" tip type catheter 102a and FIG. 2B shows a "linear" tip type catheter 102b. Both catheters 102a,b carry ring electrodes 116 for sensing the body's electrical signals and thermocouples 118 for sensing the temperature of the tip 114. The ring electrodes 116 aid the clinician in locating and verifying the sites of cardiac arrhythmia using standard intracardiac recording and in positioning the catheter to ablate the arrhythmogenic site.

The spot tip catheter 102a has a small rounded tip 114 which contacts the heart in a "spot" yielding a concentrated zone of destruction. The tip temperature is measured at an outside surface of the catheter tip.

The linear catheter 102b delivers cold along a long cylindrical tip 114 to create a line of destruction in tissue. In certain cardiac procedures, this is done to block off the effects of entire sections of the heart which could lead to atrial fibrillation, atrial flutter, or some extensive ventricular tachyarrhythmias. The temperature can be measured at an inside surface of the catheter tip. Further catheter tip structures are disclosed in co-pending and commonly assigned U.S. patent application Ser. No. 08/893,825, entitled Cryosurgical Linear Ablation Structure, filed on Jul. 11, 1997, which is incorporated herein by reference.

Figure 3:
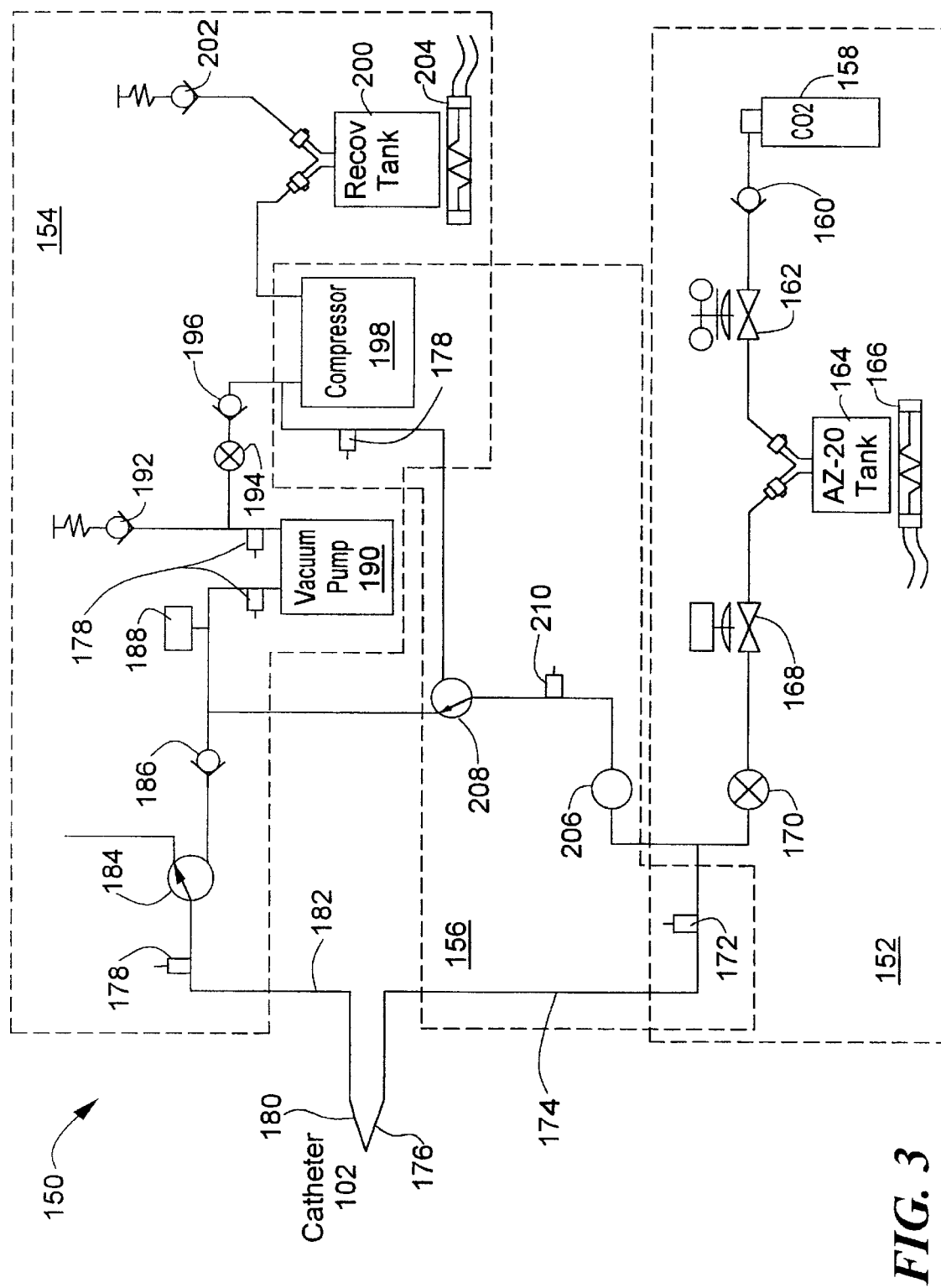
FIG. 3 is a schematic diagram of a refrigeration system that can form a part of the system of FIG. 1.

FIG. 3 shows a refrigeration system or mechanical assembly 150 that supplies refrigerant to the catheter 102. The refrigerant expands in the tip 114 of the catheter to cool it to a selected temperature. The refrigeration system 150 includes an injection section 152 for providing liquid coolant to the catheter, a recovery section 154 for recovering the vaporized coolant, and an intermediate or evacuation section 156 for evacuating refrigerant remaining in the catheter after an injection procedure is terminated.

The injection section 152 provides liquid refrigerant on demand at a high variable pressure to the catheter 102. The injection section 152 includes a source of compressed gas 158, e.g., CO2, coupled to a check valve 160. A pressure regulator 162 is coupled to the check valve 160 to bring the gas pressure down to an exemplary pressure of about 500 psia. The pressure regulator 162 is connected to a refrigerant tank 164 that holds a refrigerant, such as AZ-20 refrigerant made by Allied Signal. A load cell 166, used to measure the refrigerant level inside the tank, is placed in communication with the tank 164. A second pressure regulator 168, which is a proportional valve, is used to vary the refrigerant pressure from about 300 psia to 500 psia, for example. An injection solenoid valve 170 is coupled to the second pressure regulator 168 to turn injection on and off. A pressure transducer 172 monitors injection pressure. Umbilical tubing 174 and catheter tubing 176 provide a pathway for the refrigerant from the tank 164 to the catheter 102.

When coolant is injected into the catheter tip, the compressed gas source 158 provides about 500 psia of pressure through the check valve 160 and the pressure regulator 162 to the refrigerant tank 164. The gas pressure pushes liquid refrigerant from the tank through the proportional valve 168, through the injection solenoid valve 170, which is open, out of the console 104 and into the umbilical, and finally, into the catheter tubing.

During injection the proportional valve 168 is used to control the pressure, which is monitored by a pressure transducer 172 in the injection line which, in turn, varies the flow rate of refrigerant to the catheter tip 102. An increase in the flow rate (less restriction by the pressure regulator 168) lowers the temperature of the catheter tip. Conversely, decreasing the coolant flow rate allows the catheter tip to be warmed by its surroundings, i.e. raises the tip temperature. The proportional valve 168 is controlled by software, as described below.

The recovery section 154 provides a vacuum that creates a high differential pressure relative to the injection tube at the catheter tip 102, causing the refrigerant to rapidly change to a gas state, thereby producing a dramatic drop in the temperature of the catheter tip. The recovery section 154 also evacuates spent refrigerant from the catheter and re-condenses the vapor to a liquid state for safe storage and removal. Transducers 178 monitor the gas pressures at various points to monitor operation of the coolant recovery.

The recovery section 154 of the coolant system includes relatively large diameter catheter tubing 180 and umbilical tubing 182 coupled to a vacuum solenoid valve 184. A vacuum check valve 186 is coupled between the solenoid 184 and a flow meter 188. A vacuum pump 190 is coupled between input and output pressure transducers 178. A second check valve 192 is connected to the second pressure transducer and is also coupled to a compressor solenoid valve 194. The compressor solenoid check valve 196 is coupled to a compressor 198 for allowing refrigerant recovery in a refrigerant recovery tank 200 equipped with venting check valve 202. A load cell 204 is coupled to the tank 200.

The vacuum pump 190 and the compressor 198 run whenever electrical power is being applied to the system. If coolant is not being injected, the compressor solenoid valve 194 is closed and any air that the vacuum pump 190 has drawn in is exhausted from the system through the check valve 202. This prevents excess air from building up in the refrigerant recovery tank 200. The pressure transducer 178 and the flow meter 188 in the recovery line can detect if the catheter 102 is not connected to the system. If the catheter 102 is not connected, the vacuum solenoid valve 184 switches to atmosphere to prevent the vacuum pump 190 from pumping air, which will cause it to overheat. If the catheter 102 is connected, and coolant is not being injected, the vacuum solenoid valve 184 closes to atmosphere and opens to the vacuum pump 190, creating a deep vacuum (less than 0.2 psia) in the large diameter catheter and umbilical tubing 180,182.

When coolant injection is occurring, the compressor solenoid valve 194 is open. The vacuum in the large diameter catheter and umbilical tubing creates a large pressure drop at the tip of the catheter 102, causing the high pressure liquid refrigerant to suddenly expand into a gas and cool. The vacuum sucks the gas from the tubing, through the vacuum solenoid 184, in through the vacuum pump 190, through the compressor solenoid 194 and into the compressor 198. The gas is then compressed to an exemplary pressure of about 240 psia (at 25° C.) to liquefy it, which is then pumped into the refrigerant recovery tank 200. The check valve 202 on the tank vents off excess air that may have entered the system during catheter hookup.

The evacuation system 156 removes any refrigerant remaining in the injection line after injection has been terminated. The evacuation system 156 includes a post injection solenoid valve 206 coupled to a 3-way vent valve 208. Pressure transducers 172,210 are coupled on either side of the solenoid valve 206.

When refrigerant injection is initiated, the vent valve 208 switches from the vacuum pump 190 inlet to the compressor 198 inlet. When the injection is terminated (the injection valve closes), the post injection valve 206 opens. In this configuration, the injection lines at the outlet of the injection solenoid 170 now open to the inlet of the compressor 198. This is done because as the refrigerant is evacuated from the lines, it expands dramatically and the vacuum pump 190, under normal conditions, is not intended to handle this volume of gas. The pressure transducers in evacuation section 156 measure the line pressures.

Figure 4:
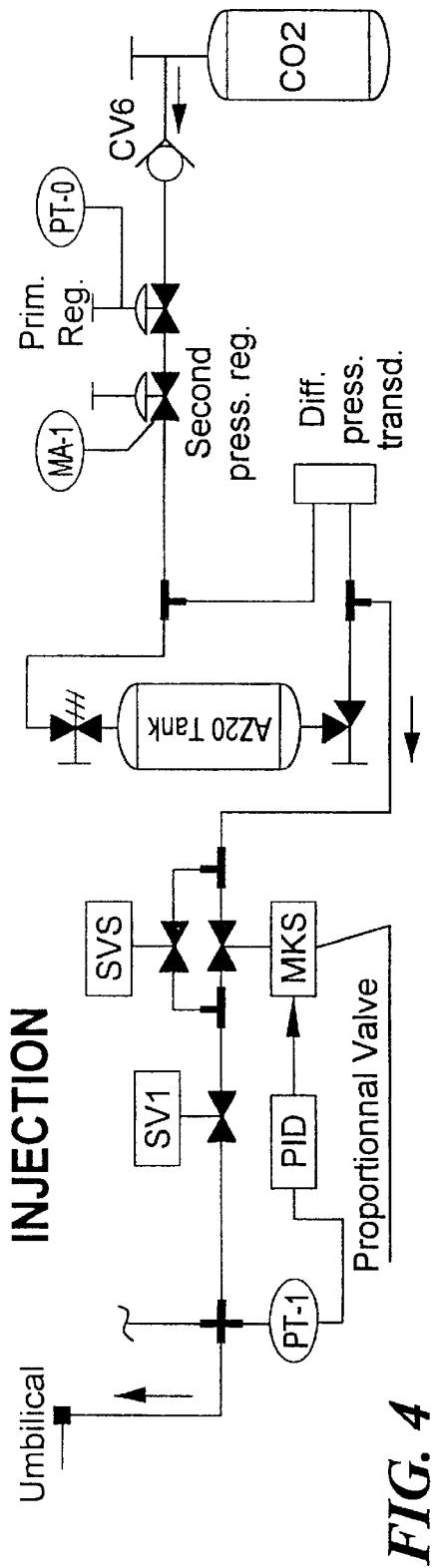
FIG. 4 is a schematic diagram of an injection section of the system of FIG. 1.

As shown in FIG. 4, another embodiment of an injection section of the cooling system includes a source of compressed gas, e.g., $CO_2$ in a tank to which a check valve CV6 is coupled. A primary pressure regulator brings the gas pressure down to about 600 psig and a secondary pressure regulator brings the pressure down to about 525 psig. Refrigerant, such as AZ-20, is stored in a tank coupled to a differential pressure transducer for measuring the coolant level in the tank.

A proportional valve is controlled by a PID (described below) for varying the coolant pressure from about 250 psig to about 500 psig. An injection solenoid valve activates the injection circuit and a pressure transducer PT1 monitors the injection pressure. When an injection of refrigerant takes place, the compressed gas provides pushes liquid refrigerant from the tank, through the proportional valve. The SV5 is open only for two seconds, to let the catheter reach high flow which increases the cooling rate, so that it takes 30 seconds or less for the temperature to reach minus 35 degrees Centigrade or colder. The refrigerant flows through the injection SV1 which is now open, out of the console and into the umbilical, and finally, into the small diameter catheter tubing.

During injection mode the proportional valve is used to vary the pressure, which is monitored by the pressure transducer PT1, and the proportional valve in the injection line varies the flow rate of refrigerant to the catheter tip. An increase in the flow rate (less restriction by the regulator) lowers the temperature of the catheter tip. Conversely, decreasing the flow rate allows the catheter tip to be warmed by its surroundings. The proportional valve can be adjusted on a console screen (mechanical monitoring) by setting the PID injection pressure and can be driven by system software in automatic mode.

During injection mode, refrigerant flows to the catheter via the umbilical for cooling tissue to a predetermined temperature. Initially valves S1, S2, S4, S5 and S6 are activated simultaneously. However, S5 is turned off about two seconds later. Valve S5 fills the umbilical injection section tube and improves the cooling rate. Software controls the pressure regulator based on the optimal position calculated by the PID temperature controller, which is described below.

Figure 5:
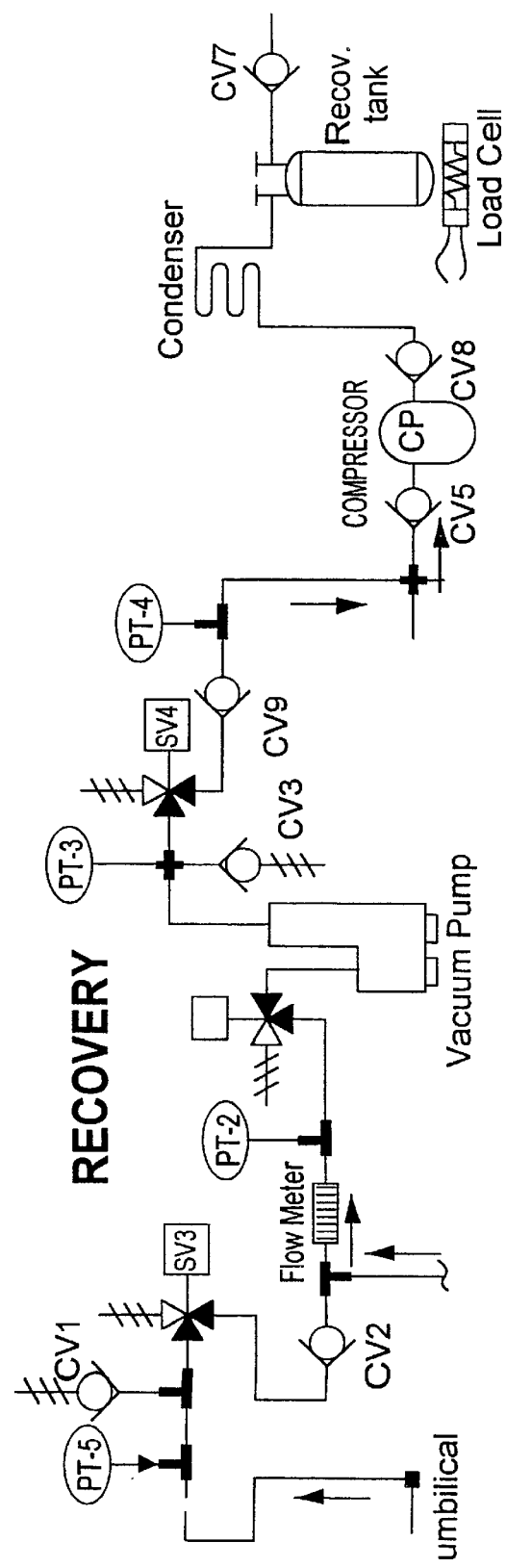
FIG. 5 is a schematic diagram of a recovery section of the refrigeration system of FIG. 1.

As shown in FIG. 5, the recovery section of the plumbing circuit serves two primary functions. The first is to provide a vacuum which creates a high differential pressure relative to the injection tube at the catheter tip. This causes the refrigerant to rapidly change to a gas state, producing a dramatic drop in the temperature of the tip. The second primary function is to evacuate the spent refrigerant from the catheter and to recondense it to a liquid state for safe storage and removal. Transducers monitor the gas pressures at various points in the recovery plumbing.

A vacuum solenoid valve SV3 has check valves CV1, CV2 coupled on either side with a mass flowmeter connected inline to monitor the flow rate. Pressure transducers PT2–5 monitor pressure at various points in the recovery section. A vacuum pump is coupled to the compressor and a condenser is coupled to the compressor to facilitate coolant recovery into the recovery tank.

The vacuum pump and compressor are running when electrical power is applied to the system. If an injection of refrigerant is not taking place, the compressor solenoid valve SV4 is closed and any air that the vacuum pump may draw in is exhausted from the system through the solenoid valve SV4. This prevents excess air from building up in the refrigerant recovery tank. A pressure transducer and a flowmeter in the recovery line can detect if a catheter is not connected to the system. If a catheter is not connected, the vacuum solenoid valve SV3 switches to atmosphere to prevent the vacuum pump from pumping air, which will cause it to overheat. If a catheter is connected, in the no injection "idle" mode, the vacuum solenoid valve closes to atmosphere and opens to the vacuum pump, creating a deep vacuum (less than 0.5 psia) in the catheter and umbilical tubing.

When an injection takes place, the compressor solenoid valve opens. The vacuum in the catheter and umbilical tubing creates a large pressure drop at the tip of the catheter, causing the high pressure liquid refrigerant to suddenly expand into a gas and cool. The vacuum sucks the gas from the tubing, through the vacuum solenoid SV3, in through the vacuum pump, through the SV4 and into the compressor. The gas is then compressed until at about 240 psig (at 25° C.), it liquefies through the condenser and is pumped into the refrigerant recovery tank. There is a 350 psig check valve on the tank that vents off CO2 and excess air that may have entered the system during catheter hookup. The refrigerant tank level, measured by the load cell, is considered "full" when it is 80% full of liquid refrigerant.

After injection, the evacuation section is activated to evacuate the refrigerant from both the umbilical tubes. Valves S1, S5 and S6 are inactive during evacuation while valves S2, S4, and S3 are active. The watchdog system, which is described below, closes the pressure regulator.

Figure 6:
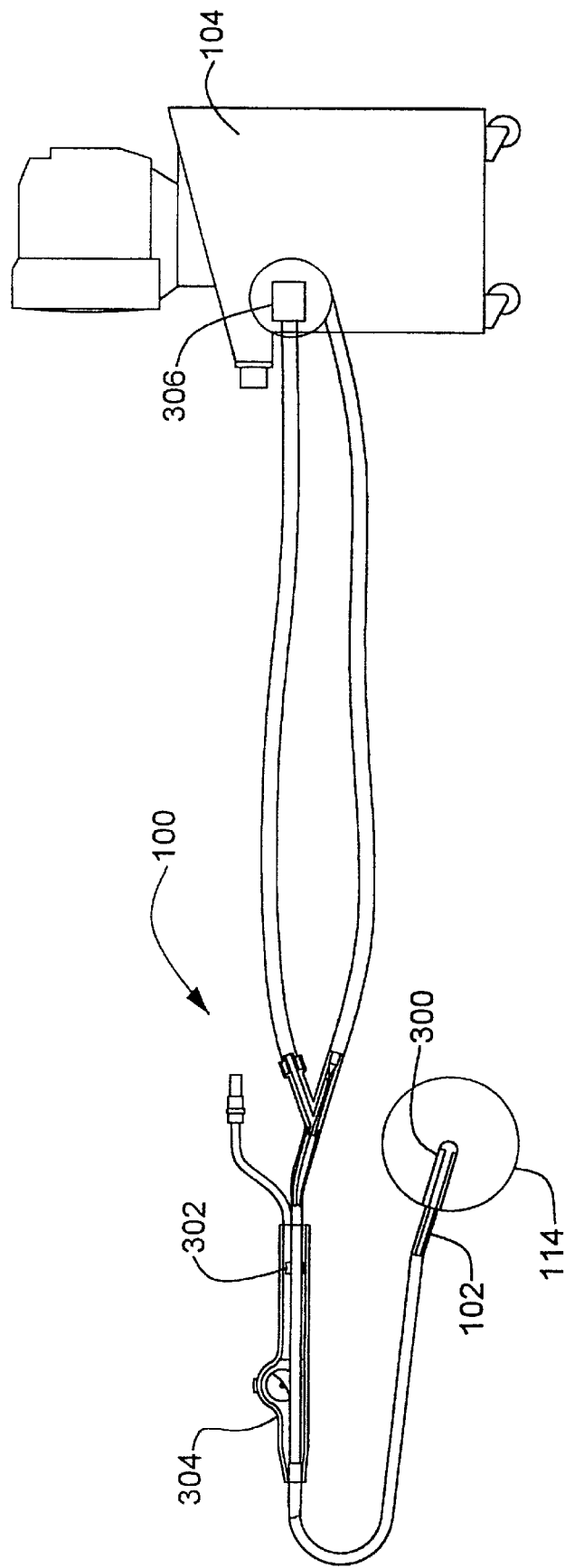
FIG. 6 is a schematic diagram of the system of FIG. 1 having a leak detection system.

FIG. 6 shows the cryogenic catheter system 100 having a leak detection system for detecting a fluid, such as blood, within the closed coolant flow network. The leak detection system includes a first sensor 300 located in the catheter tip 114. The first sensor 300 detects the presence of blood internal to the catheter tip 114. In an exemplary embodiment, the first sensor 300 measures the impedance between a dummy wire inside the catheter and the catheter tip. If the impedance is outside a predetermined range, the first sensor 300 provides a blood detection signal to the console, which then stops the flow of injection fluid but maintains the coolant vacuum.

The leak detection system further includes a second sensor 302 located in the catheter handle 304 for detecting blood within the coolant stream. In one embodiment, the second sensor 302 is an optical type sensor. Upon detecting blood in the coolant, the second sensor 302 provides an indication to the console 104, which then terminates vacuum pressure on the coolant to prevent blood from being removed the patient.

The leak detection system can also include a third sensor 306 located in the console 104 in communication with the coolant return path. When the third sensor 306 detects a liquid, such as blood, within the coolant recovery path, the console 104 terminates vacuum pressure to prevent the blood from reaching the vacuum pump 190 (FIG. 3).

Figure 7:
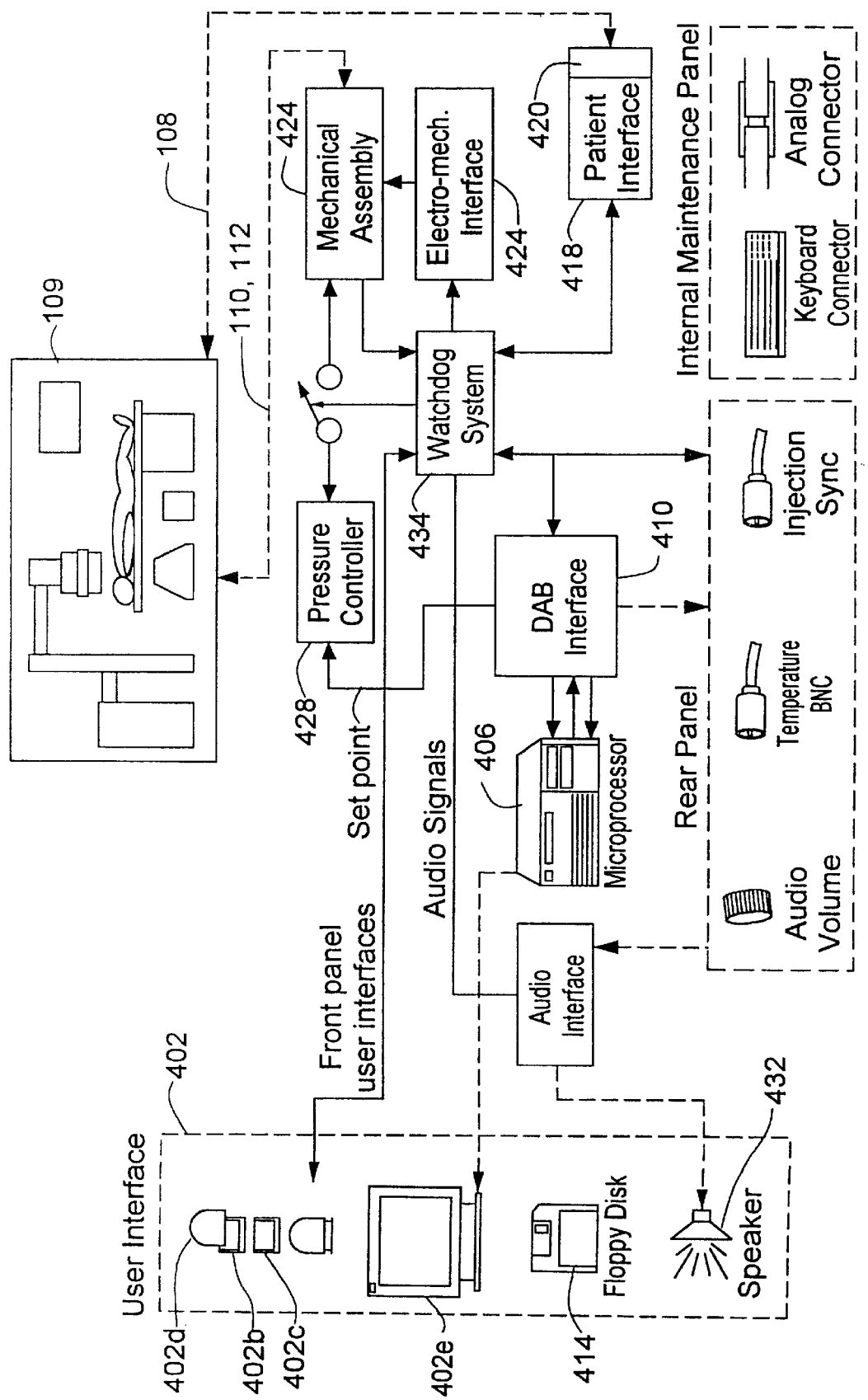
FIG. 7 is a pictorial and schematic diagram of console components.

FIG. 7 shows an exemplary embodiment of the console 104 having an LCD touch screen that displays console status and data, and accepts user data and control inputs. Various discrete indicators, controls, and displays show console status and allow inputs for manual system operation. In an exemplary embodiment, a user interface 402 includes a start (injection) button 402b allows the injecting refrigerant into the catheter and a stop (injection) button 402c stops the delivery of refrigerant. The stop injection button 402c overrides software control in automatic mode, thus acting as an emergency backup control. An injection on light 402d illuminates when the start injection button 402b is pressed and remains illuminated until refrigerant injection is stopped. An LED temperature readout 402e displays the actual catheter tip temperature as measured by a thermocouple 118 (FIG. 2B) located in the catheter tip. The LED display independently confirms the temperature displayed on the touch screen.

A standard ISA bus 404 is coupled to a CPU 406, a touch screen control 408, and a data acquisition interface (DAI) 410, along with various peripheral devices, such as a hard disk 412 and a floppy disk 414. The DAI 410 contains signal conditioning circuits required for conveying information to the CPU 406. The CPU 406 acts as a graphical display controller, patient data processor, and controller for automatic operation modes. A patient interface 418 is coupled to the data acquisition interface 410, and is connected to the catheter 102 through a patient overload protection module 420 and an ECG connection box 422. The patient interface 418 transmits system operating parameters including catheter tip temperature, catheter type (spot/elongate) and connection status across an electrical isolation barrier and ultimately to the CPU 406.

An electro mechanical interface 424 contains various driver circuits for the controlling components, e.g., valves, in the mechanical assembly 426, e.g., the refrigeration system 150 (FIG. 3), and driver circuits for interfacing to the front panel controls & indicators box 402. A PID controller 428 generates a control voltage to drive the proportional valve 168 to control the pressure in the mechanical assembly 424 (refrigeration system 150, FIG. 3).

An audio generator 430 synthesizes audio tones that correspond to pressing panel control keys, injection status on, and console warnings or failures. The audio generator activates a speaker 432 that generates the sounds corresponding to the audio tones.

A watchdog system 434 is coupled to the mechanical assembly 426 via the electromechanical interface 424. The watchdog system 434 receives data from the data acquisition interface 410 for generating control signals for the mechanical assembly 426. In an exemplary embodiment, the watchdog system 434 directly controls the injection valve 170 (FIG. 3), the vent valve 208, and the vacuum valve 184 in the mechanical assembly. The watchdog system 434 also monitors console status and generates warning and failure signals and controls failure states of the mechanical assembly. In an exemplary embodiment, the watchdog system 434 is implemented in a field programmable gate array (FPGA). By having a circuit module control the mechanical assembly 426 instead of the CPU, patient safety is enhanced since the watchdog system 434 is not subject to software crashes and unknown states.

Figure 8:
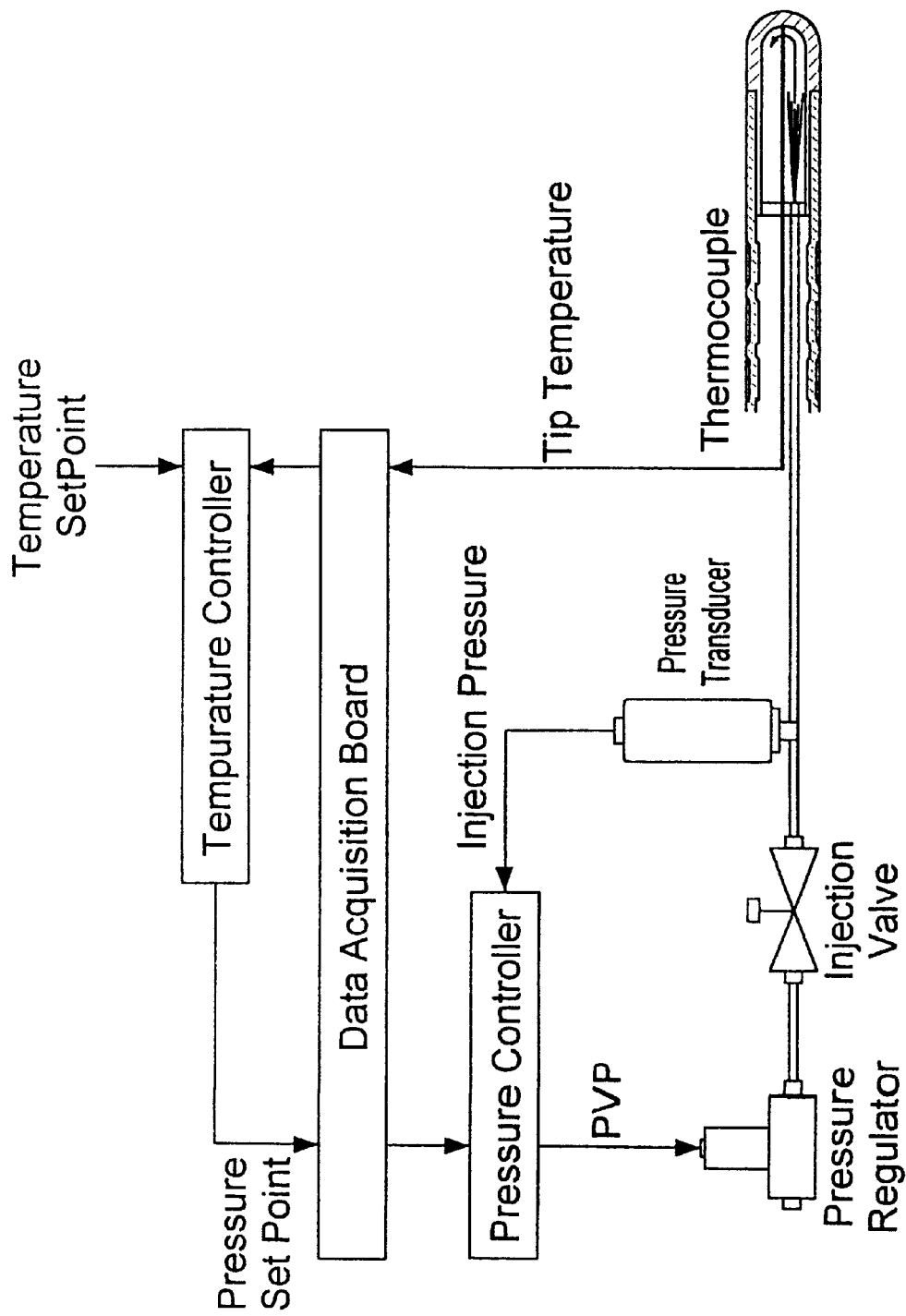
FIG. 8 is a schematic block diagram of a temperature control system of the console.

FIG. 8 shows an exemplary implementation of the pressure control circuit. The pressure controller circuit includes a PID used to control the proportional valve. This valve controls the injection pressure which enables the system to operate at pressures ranging from 250 to 500 psig. A pressure transducer PT-1 is mounted at the outlet of the injection valve SV1. The sensor PT-1 output and the requested temperature set point are fed to a differentiator. The difference signal activates an integrator which in turn activates a driver of the proportional valve.

During a "cryo-ablation mode" the delivery pressure is set to fixed set point of 500 psig. During a "cryo-mapping mode" when a spot catheter is used, the system controls the delivery pressure of the refrigerant in order to reach and maintain a selected temperature. This continuous temperature control assures compensation of the heat load changes due to the blood movement during a cardiac cycle or due to changes in the adhesion between the catheter tip and the tissues.

Tip temperature control is performed using two control loops, a hardware pressure control loop and a software temperature control loop. Software controls the tip temperature by reading the current tip temperature via a thermocouple and determines the required delivery pressure setpoint using a PID algorithm based on digital proportional-integral-derivative (PID) compensator. The pressure set point is sent to the hardware pressure controller, which assures continuous control of the proportional valve based on a pressure transducer reading.

Should the software fail, a redundant hardware system is implemented as part of the watchdog system to monitor the pressure setpoint sent by the software. This feature insures that the set point will never exceed the allowable operating pressure of 500 psig. Furthermore, the Watchdog system monitors the state of the CPU and the software in order to detect a freezes or abnormal loops and takes action on kicking the mechanical plumbing into a safe mode. Another important feature of the Watchdog system is to block the analog setpoint controlled by the CDM whenever an injection OFF is requested or a failure is generated.

Figure 9:
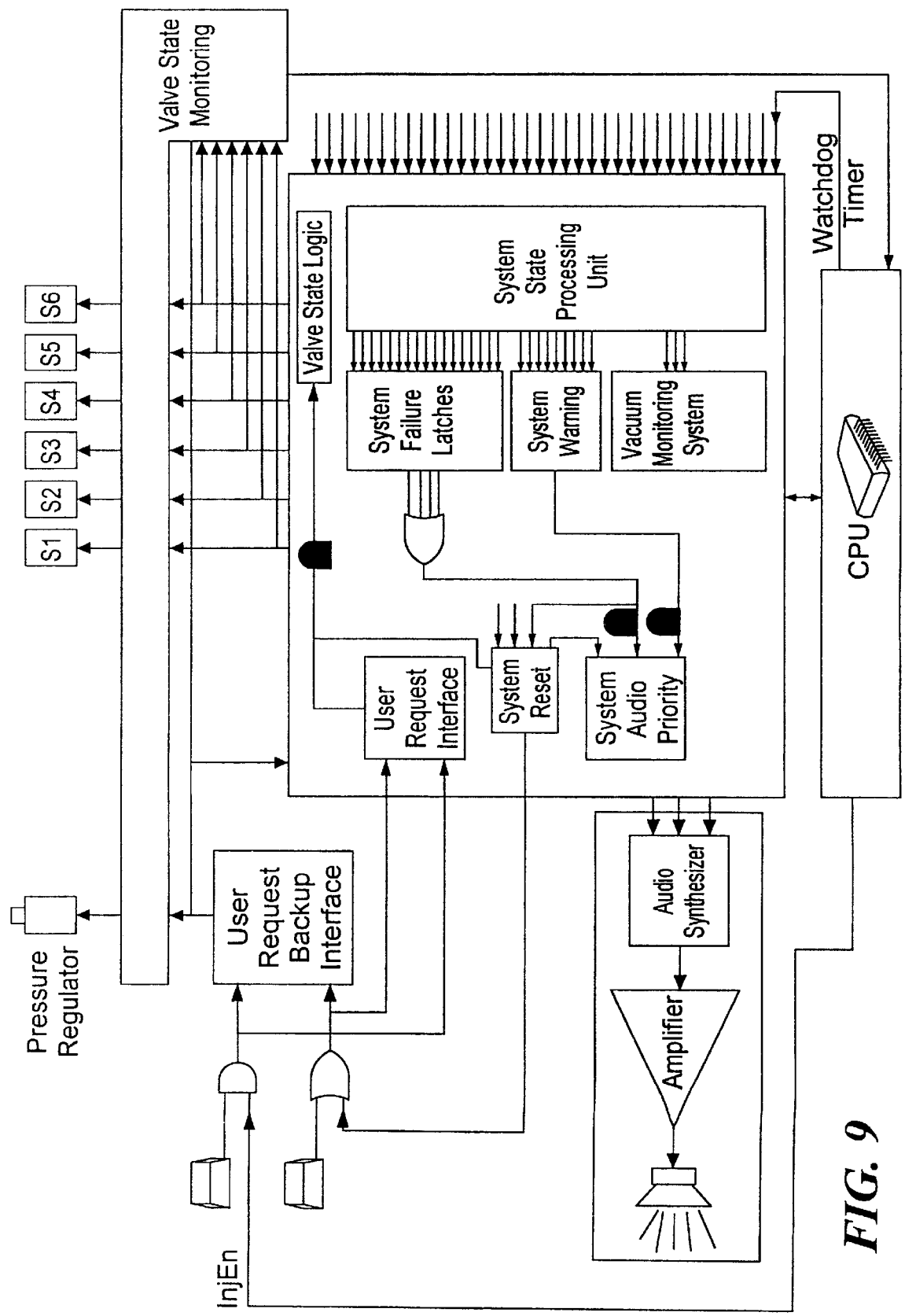
FIGS. 9 and 10 are schematic block diagrams of watchdog system of the console.
Figure 10:
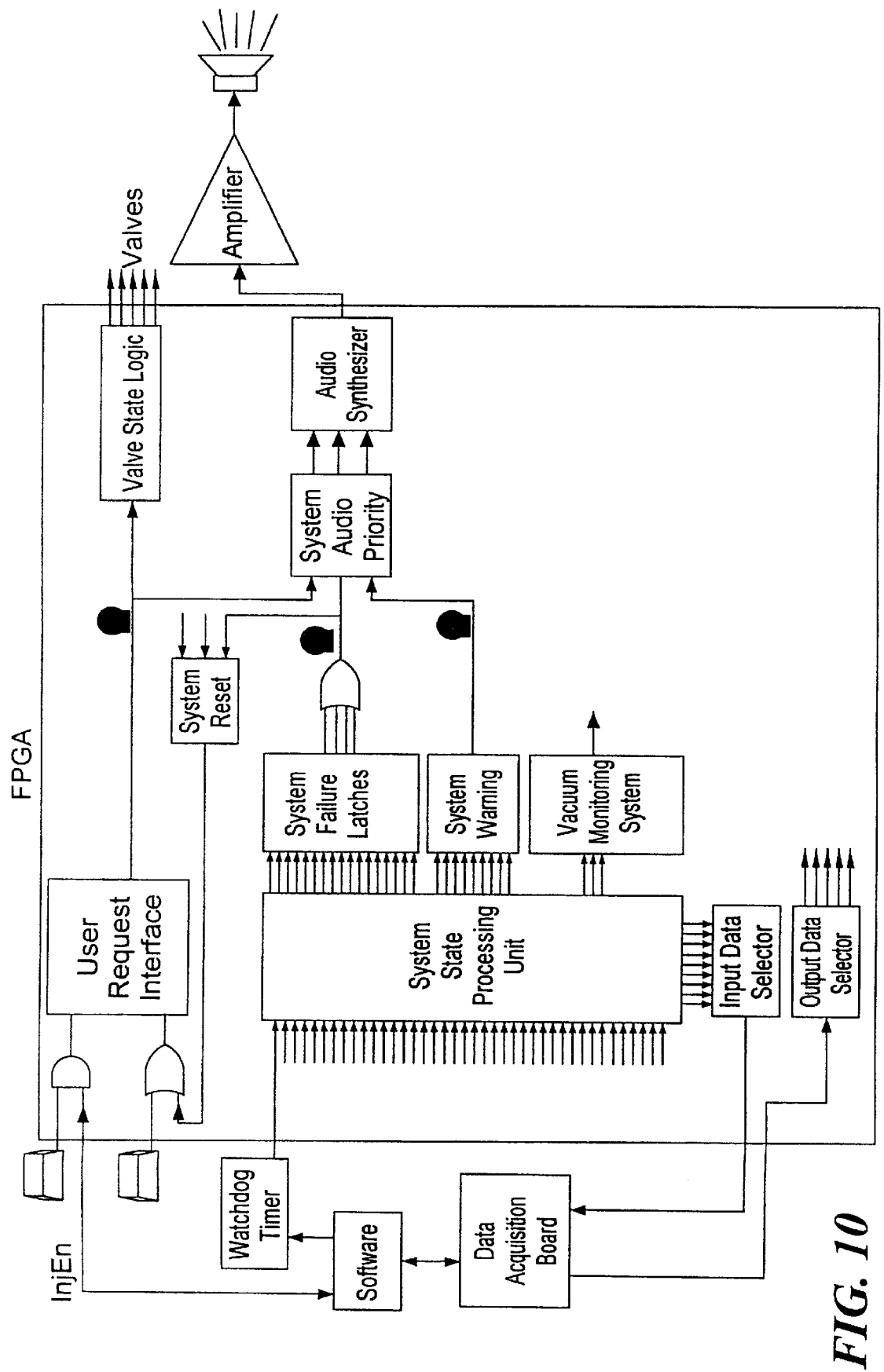
Figure 11:
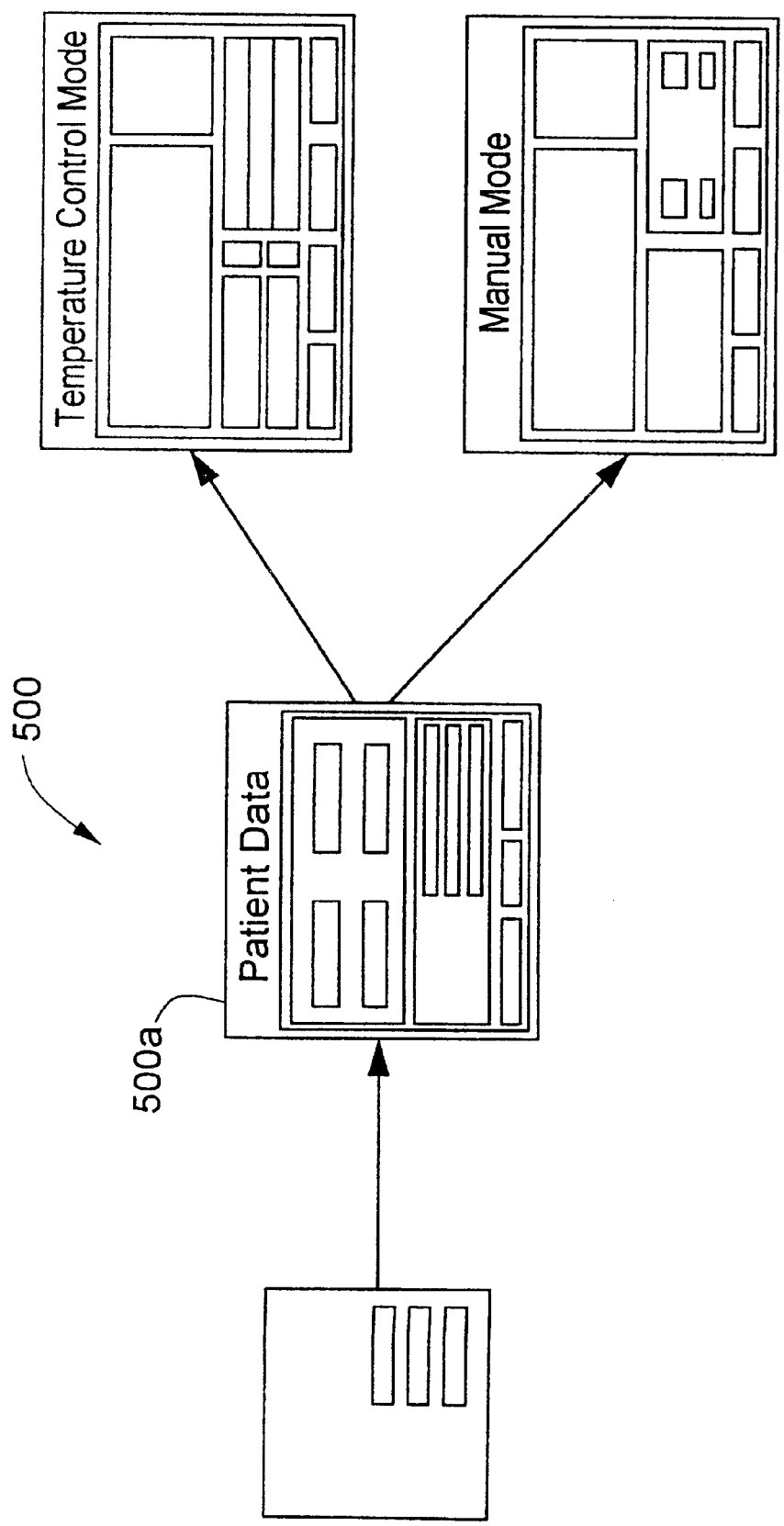
FIG. 11 shows exemplary procedure panels for being shown on a display that forms a portion of the console.
Figure 12:
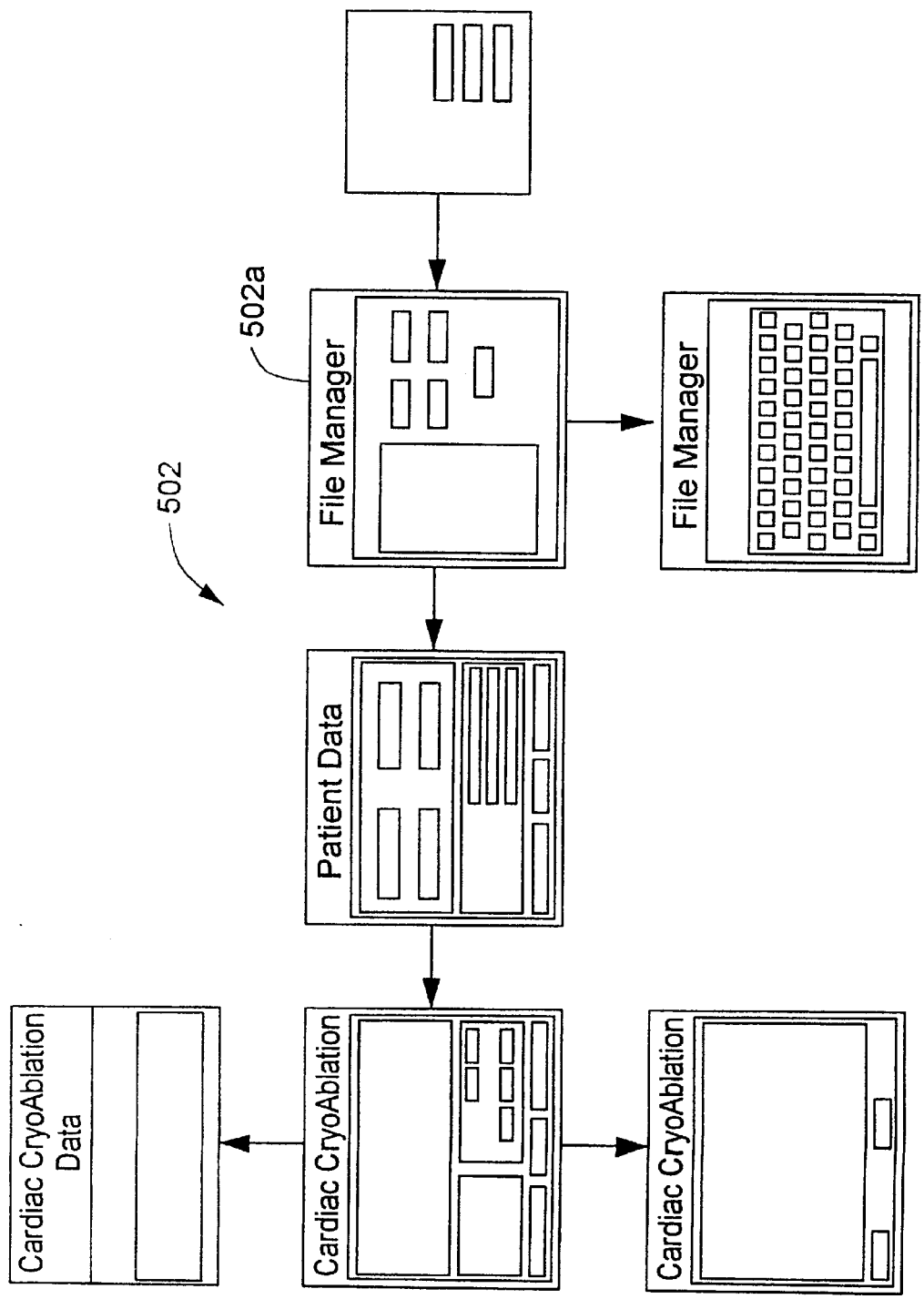
FIG. 12 shows exemplary recall panels for being shown on a display.
Figure 13:
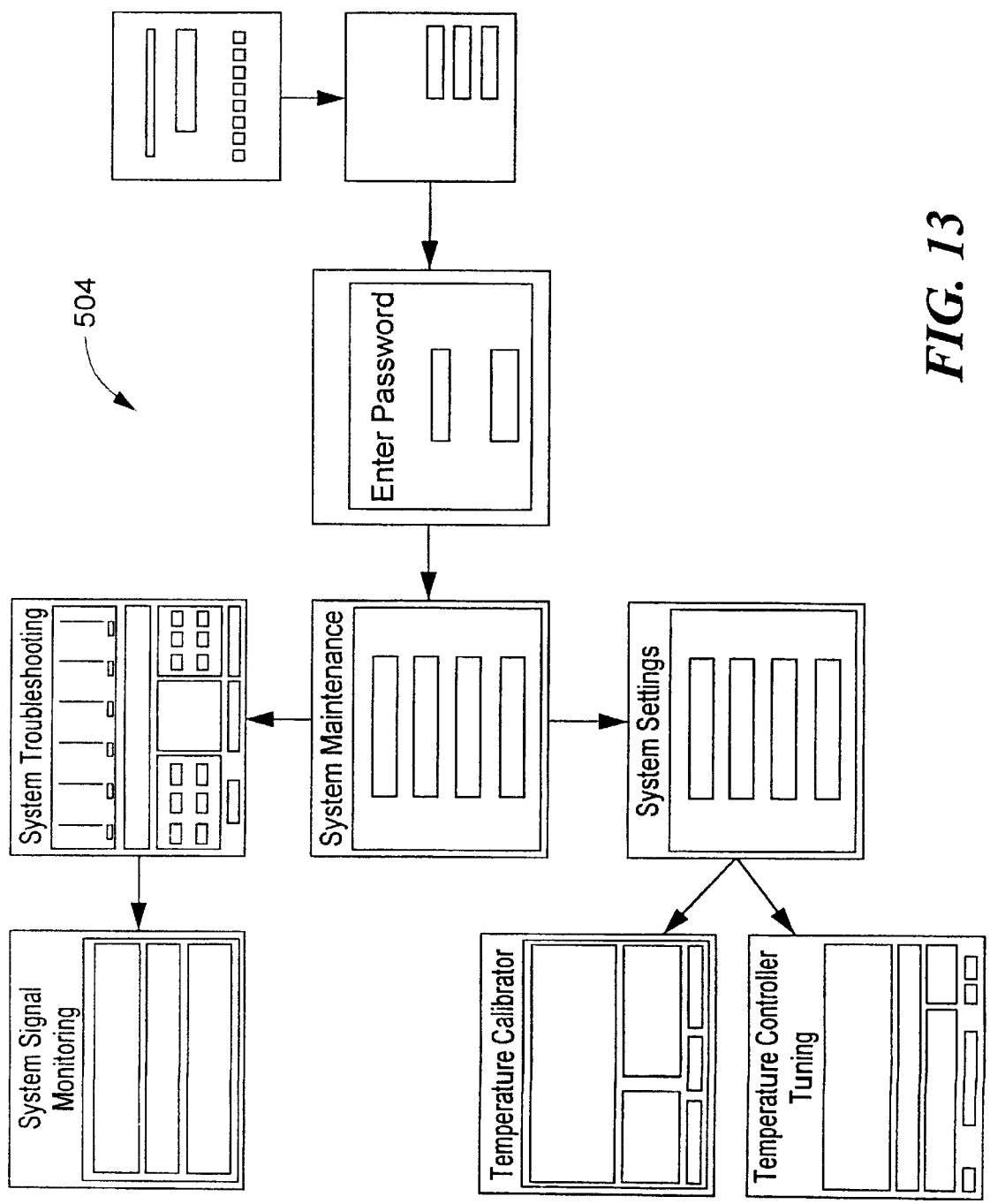
FIG. 13 shows exemplary maintenance panels for being shown on a display.
Figure 14:
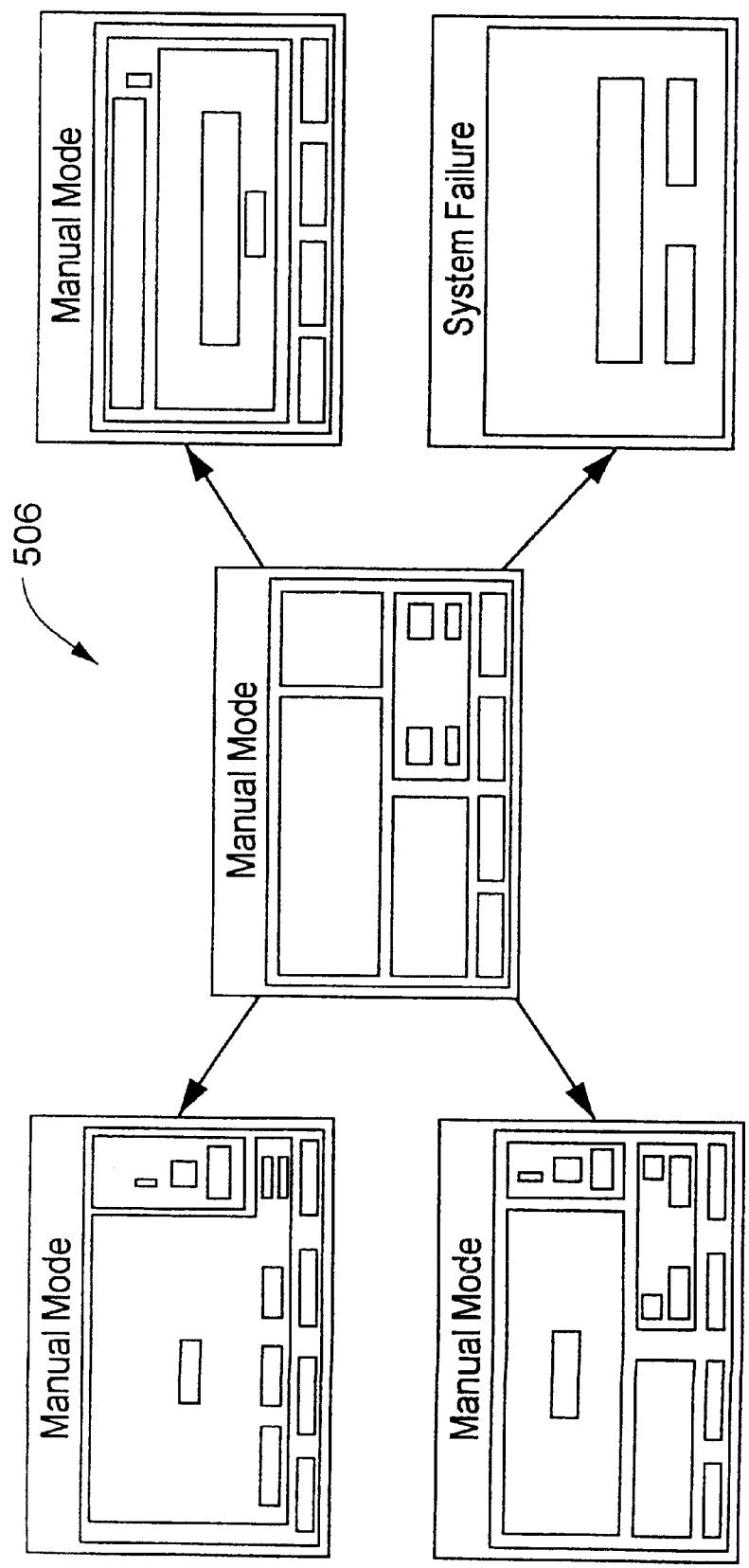
FIG. 14 shows exemplary warning/failure panels for being shown on a display.

FIGS. 9 and 10 show an exemplary configuration for the watchdog system including a Field Programmable Gate Array. The watchdog system monitors both injection and vacuum functions for failures and degraded operational performance of the mechanical plumbing in order to safely start and end the procedure at any time. The injection valve is controlled only through the Watchdog system. The only control that software would act over the injection valve is to turn OFF the injection when automatic timing is requested.

The Watchdog system processes information acquired from system and generates failures and warnings. Warning alerts are generated when patient safety is not compromised and the procedure can be continued. Failure alerts are generated when patient safety is potentially compromised and the system puts itself into a Safe Mode State. For each failure or warning, the system can provide an automatic safe system default, a visual indication light, an audible alarm, and a visual informative message on the screen.

The watchdog system is a combination of discrete circuits and a FPGA chip. The FPGA processes the failures and warnings and controls the electromechanical valves based on the user requests. Redundant circuits around the FPGA prevent a single fault hazardous failure of this device. A user request backup circuit receives the same user requests from the user interface controls and produces the same action that the FPGA would produce. This redundant circuit insures that the injection stops when an injection OFF is requested in both cases when the FPGA or the backup circuit fails to respond.

A second redundant circuit is designed with discrete component and used to monitor the valve control lines that are set by the FPGA. This circuit compares FPGA output lines to a set of predefined values based on the system State and insure that the FPGA is sending the right valve sequence. Should a valve sequence not match the predefined values a failure is generated and a message is sent to the software in order to warn the user.

An independent external watchdog timer is implemented on the CPU board to monitor the software and CPU status which secure the system uses in case a software freeze. A control line is sent to the FPGA indicating a software or CPU freeze.

The FPGA processes signals supplied from different parts of the system in order to determine the state of the system and provide control lines to the valve interface circuit. Should an alert condition be captured, the FPGA generates and prioritizes audio signals. The software communicates with this device through the data acquisition board.

External to the FPGA chip, the electromechanical transducer outputs are fed to a block of comparators which compare the current transducer value to a predefined threshold. The input block of the FPGA includes the system state processing unit, which process the status lines. The output lines of the processing unit are fed to a failure/warning unit which determine if the condition result is a failure or warning based on the user request.

The second block is the failure latch block which receives all processed condition lines and feeds them to a large OR gate. The latch block allows the capture of fast abnormal events. Failure, warning and other functional lines are fed to a priority selector block which processes the signal origin and prioritizes the audio signals. Failure audio signal has the highest priority. The audio signal is fed to the audio synthesizer, which produces the audio enable/disable signals that are sent to audio circuit.

Another function of the FPGA is to generate the system states (FIGS. 9–10) and control the electromechanical valves based on the user requests. Prior to the valve control, the FPGA verifies the hardware and system status and sets the valve control lines.

When user request an injection, the FPGA verifies the failure/warning lines before any action is transmitted to the valves. Once the user request is accepted the valve control block sets each valve to the appropriate position and sets the appropriate audio tone.

Another function of the FPGA is to provide an input/output port to the software. When a warning or failure is generated, the software acquires the information regarding the alert through an input data selector which provides access to all condition lines as processed by the system state processing unit. An output data selector is implemented inside the FPGA which allows to increase the number of digital output lines provided by the data acquisition board.

The cryogenic catheter system 100 includes software, which is executed by the CPU 406, for controlling the overall operation of the system by acquiring data from the system hardware components, for saving data on the system hard disk, and displaying data on the system display screens. At system start up, the software initiates the hardware components and begins a system self test.

FIGS. 11–14 show exemplary display panels for allowing a user to select a desired action for the system. After start up, a user is allowed to select one of three options on the touch screen 400. More particularly, the user can instruct the software to access a procedure panel 500, a recall panel 502, or a maintenance panel 504. In addition, a failure/warning panel 506 is displayed upon detecting a system fault.

By selecting the procedure panel 500 (FIG. 11), the display 400 shows a patient data panel 500a where patient information is entered and saved to the hard disk. Through this panel 500 the user will be able to choose the type of procedure to run. The options include a "spot" procedure in either manual or automatic mode, or a "linear" procedure which is only available in manual mode. During the selected procedure, the software continuously displays certain information on the touch screen 400 and saves temperature profile information to the hard disk for future recall. If a system failure is detected during the procedure, the software will stop saving the temperature profiles and open a separate file where it will log the current state of the system.

If the recall panel 502 (FIG. 12) is selected, a file manager panel 502a is displayed. This allows the user to select from the list of previously run procedures. The selected file may then be opened for viewing, copied to a floppy disk, or deleted from the hard disk.

The maintenance panel 504 (FIG. 23) aids maintenance personnel in performing routine system maintenance and to help technical personnel in troubleshooting system failures. To prohibit unauthorized personnel from accessing low level system information, certain troubleshooting panels can be password protected.

The warning/failure panel 506 (FIG. 14) displays warning and failure information when a system fault is detected, as described above in connection with the watchdog system 434. Exemplary warning and failure conditions are listed below in Table 3.

The system protects the patients from unsafe conditions while allowing the system to operate in the presence of warning conditions that do not compromise patient safety. The watchdog system monitors the umbilical electrical connections from the catheter to the console. If continuity is lost and injection is Off, the system generates a warning. Should the user ignore the warning message and try to initiate an injection a failure is generated and injection is disabled. If the continuity is lost and injection is On, the system generates a failure and stops injection.

The system monitors the injection connectors at both the console and catheter side by measuring the baseline flow of the system. Should a baseline flow higher than 150 sccm be detected a warning is generated. FIG. 26 graphically shows flow rate conditions. The system detects if either side is not connected and disables injection. If either side is not connected and injection is Off, the system generates a warning. Should the user ignore the warning message and try to initiate an injection a failure is generated and injection is disabled.

The system also monitors the vacuum connections at both the console and catheter side. If either side is not connected, the system disables the injection. If either side is not connected and injection is OFF, the system generates a warning. Should the user ignore the warning message and try to initiate an injection a failure is generated and injection is disabled. If either side is not connected and injection is ON, the system generates a failure and stops injection.

Since the system uses thermocouples to measure the tip temperatures, the integrity of the electrical connection is verified each time the electrical connection of the catheter is connected to the console. Lack of electrical connector integrity could happen during or after sterilization/shipping process or by an improper pin configuration. Detection is done through the software, which acquires the distal and proximal temperatures. Should the tip temperature reading be less than +30 C or higher than +45° C., the system can display a message, disable the procedure panel, and/or disable injection.

In order to assure that software display and control functions of the console are appropriate to the type of the catheter, the cryoablation system recognizes the type of cryoablation catheter, which is connected to the console, and then compares catheter type to the selected software panel. If catheter type is not compatible with the selected software panel, the system displays a message, locks out the procedure panel and disable injection.

The system also monitors baseline coolant flow. Baseline flow is defined as the vapor flow measured at the inlet of the vacuum pump when both mechanical umbilical tube are connected to the catheter and console and the injection is OFF. Since the system is not perfectly leak tight, a small baseline flow always exists. The maximum allowable baseline flow is 150 sccm. When a high baseline flow is detected, the system generates a warning. Should the user ignore the warning message and tried to initiate an injection request, the system switch from warning mode to a failure mode.

Refrigerant vapor flow is measured at the inlet of the vacuum pump. If the flow is outside predefined parameters, a failure is generated. This implies that refrigerant is being lost somewhere because of a variety of possible failures, including but not limited to abnormal refrigerant recovery. This detection is performed by comparing the actual vapor flow curve to a predefined flow curve specific to each type of catheter. The comparison is done point to point which provides a in real time detection.

When an excessive refrigerant flow is detected a failure is generated and injection is stopped and refrigerant is recovered from the catheter. The threshold of the excessive flow is specific to each catheter type.

The system constantly monitors the catheter tip temperature during the mapping mode when only a spot catheter is used. Should the tip temperature drops below −47° C. during cold mapping the system automatically stops the injection and generates a failure. The system constantly monitors the catheter tip temperature during the ablation mode when both catheter types are used. Should the tip temperature not drop below −50 C after 75 seconds of injection, the system generates a warning message indicating that the current temperature is minimum reachable temperature and the clinician has the choice to stop relocating the catheter or continue if clinical effect occurred.

As described above, a leak detector is built in to the tip of the catheter provided by CryoCath. A high impedance exists between the catheters active electrode and the common point of the catheters thermocouples. If blood enters the catheter tip, this impedance drops substantially. If a leak is detected during a procedure, the system stops injection, maintains vacuum in order to draw back the refrigerant vapor, and produces a system failure indication The system also detects blood in the catheter handle. If blood is detected during a procedure, the system stops injection, stops the vacuum in the umbilical, and produces a system failure indication.

The system has three tanks that are monitored all the time and the user is warned when abnormal tank capacity is presented. Tank capacities are designed in a manner that they match each other which, allow tank changes to be done at the same time. The watchdog system monitors tank levels during the procedure and the software checks these levels at system power up in order to prevent the necessity of changing tanks during a procedure.

The system has two operative threshold detection stages. At power-up, if there is insufficient capacity for one procedure, injection must be disabled so a procedure cannot begin. The system will not function until the appropriate tanks are replaced. Furthermore, should a tank level drop below the operative threshold during a procedure, a warning signal is generated informing the user that he is able to continue the procedure, however the appropriate tanks must be replaced prior to the next procedure. If the level progresses to the point where it cannot support the current procedure, a failure is to be generated and the procedure must be terminated.

A full procedure for the Spot Lesion Catheter is defined as 20 injections ×2 minutes @ 700 sccm for cold mapping and 10 injections ×5 minutes @ 1200 for ablation. For example, at this rate a full 6.5 lb tank treat four patients. A full atrial flutter procedure for the 25 mm Linear Catheter is defined as 10 injections ×5 minutes @ 2800 sccm. For example, at this rate, a full 6.5 lb tank treat four patients.

When the gas pressure drops below 650 psig (±5 psig), the system produces a failure and disable injection if detected during power-up testing, produces a warning if detected during a procedure. When the gas pressure drops below 525 psig (±5 psig ), a failure is produced which disables injection, thus stopping the procedure.

When the level of refrigerant drops below 20% (±1%) of tank capacity, the system produces a failure and disable injection if detected during power-up testing, produces a warning if detected during a procedure. When the level of refrigerant drops below 5% (±1%) of tank capacity, a failure be produced which disables injection, thus stopping the procedure.

When the level of refrigerant rises above 60% (±1%) of tank capacity, the system produces a failure and disables injection if detected during power-up testing, produces a warning if detected during a procedure. When the level of refrigerant rises above 78% (±1%) of tank capacity, a failure be produced which disables injection, thus stopping the procedure.

If liquid is detected in the vacuum line, the system stops injection, stops the vacuum and produces a system failure indication.

The system further monitors the vacuum pump and the compressor for malfunctions, as well as software for freezes. Should the software freezes for more than 2 seconds, the watchdog timer generates a signal to the FPGA.

During injection, the temperature of the refrigerant at the console needs to stay below a maximum value. For AZ-20, this maximum temperature is 30° C. If the refrigerant temperature is too warm, the refrigerant is more susceptible to the formation of gas bubbles during mapping mode, this is due to the increase of the critical temperature of the refrigerant. These bubbles, when moving past the catheter tip, cause the temperature of the tip to oscillate around the preset temperature, thus affecting the cooling power of the tip. The system monitors the temperature of the liquid refrigerant at the console procedure panel during injection. If the temperature rises above 30° C., the system stops the injection and creates a failure Electro-mechanical valve monitoring is provided to ensure proper functioning of the mechanical system. Should a valve fail, the FPGA stops the injection and evacuates the umbilical lines.

Built-in temperature references check if the temperature measurement is working properly, and if the calibration equation is still within ±2° C. This test is done one time when the console is turned ON and during the power up test. Should the temperature calibration checking fail, this software looks the access to the procedure panels and the procedure cannot be started.

The system 100 can monitor system operation through testing during power-up and from hardware. The system operates in the presence of a problem during a procedure unless patient safety is compromised. That is, a procedure in progress is allowed to finish unless there is a risk to the patient by continuing the procedure. If, however, a failure is detected when power is first applied, the user is not allowed to begin a procedure with a known failure present. This is controlled with the enabling of the injection valve 170 (FIG. 3), which delivers refrigerant to the catheter 102. The injection valve 170 is not enabled until power-up tests have been successfully completed. If any test fails, the valve 170 is not enabled and pressing the injection on button has no effect.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A cryogenic catheter system, comprising:
   a cryogenic catheter having a tissue-treating end and a mating end;
   an umbilical system having a first end coupled to the mating end of the catheter and a second end:
   a console coupled to the second end of the umbilical system, and a processor coupled to the console for controlling a pressure of fluid coolant flowing to the catheter, controlling a vacuum pressure of gas coolant flowing from the catheter or implementing a user selected treatment procedure, an monitoring system operating and safety parameters wherein the processor regulates coolant flow and vacuum operation to maintain a pressure within the cryogenic catheter below a patient's blood pressure.

2. The system according to claim 1, further comprising a leak detection system.

* * * * *